United States Patent [19]
Jaeggi

[11] Patent Number: 5,162,310
[45] Date of Patent: Nov. 10, 1992

[54] PHENYLALIPHATYLAMINOALKANEDI-PHOSPHONIC ACIDS

[75] Inventor: Knut A. Jaeggi, Basel, Switzerland

[73] Assignee: Ciba-Geigy Corporation, Ardsley, N.Y.

[21] Appl. No.: 437,484

[22] Filed: Nov. 15, 1989

[30] Foreign Application Priority Data

Nov. 28, 1988 [CH] Switzerland .................. 4404/88

[51] Int. Cl.$^5$ .................. C07F 9/38; A61K 31/045; A61K 31/66
[52] U.S. Cl. .................. 514/107; 562/13
[58] Field of Search .................. 562/13; 514/107

[56] References Cited

U.S. PATENT DOCUMENTS

| | | | |
|---|---|---|---|
| 3,683,080 | 8/1972 | Francis | 424/204 |
| 4,927,814 | 5/1990 | Cole et al. | 562/13 |

FOREIGN PATENT DOCUMENTS

| | | |
|---|---|---|
| 170228 | 2/1986 | European Pat. Off. |
| 186405 | 7/1986 | European Pat. Off. |
| 224751 | 6/1987 | European Pat. Off. |
| 0252504 | 1/1988 | European Pat. Off. |

OTHER PUBLICATIONS

Derwent Abstract 88-008486/02 of EP 252504.
Abstract of EP-272208 & corresponding N08704860, Derwent No. 88-169460/25.

*Primary Examiner*—Joseph E. Evans
*Attorney, Agent, or Firm*—Irving M. Fishman; Karen G. Kaiser

[57] ABSTRACT

Phenylaliphatylaminoalkanediphosphonic acids of the formula

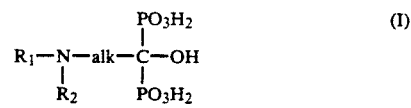

in which $R_1$ is an aliphatic hydrocarbon radical having 4 and not more than 7 C atoms and substituted by phenyl, $R_2$ is a monovalent aliphatic hydrocarbon radical having 1 and not more than 4 C atoms and alk is a divalent aliphatic hydrocarbon radical having 2 and not more than 4 C atoms, and their salts, have a particularly pronounced regulating action on calcium metabolism and can be used as medicaments for the treatment of diseases to be attributed to disturbances thereof. They are prepared, for example, for reacting a compound of the formula

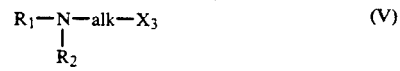

in which $X_3$ denotes carboxyl, with a phosphorylating agent and hydrolyzing the primary product.

7 Claims, No Drawings

PHENYLALIPHATYLAMINOALKANEDIPHOSPHONIC ACIDS

The invention relates to phenylaliphatylaminoalkanediphosphonic acids of the formula

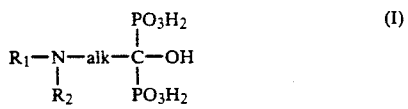

in which $R_1$ is an aliphatic hydrocarbon radical having 4 and not more than 7 C atoms and substituted by phenyl, $R_2$ is a monovalent aliphatic hydrocarbon radical having 1 and not more than 4 C atoms and alk is a divalent aliphatic hydrocarbon radical having 2 and not more than 4 C atoms, and their salts, processes for the preparation of the compounds according to the invention, pharmaceutical preparations containing these and their use as medicament active ingredients.

Examples of aliphatic hydrocarbon radicals $R_1$ substituted by phenyl are phenyl-$C_4$-$C_7$-alkyl or phenyl-$C_4$-$C_7$alkenyl radicals. Examples of monovalent aliphatic hydrocarbon radicals are $C_1$-$C_4$alkyl or $C_2$-$C_4$alkenyl radicals, and examples of divalent aliphatic hydrocarbon radicals are, in particular, $C_2$-$C_4$alkylene radicals.

Lower radicals and compounds below are to be understood as meaning, for example, those having not more than 7, in particular not more than 4, C atoms. The general terms moreover have, for example, the following meanings:

$C_1$-$C_4$alkyl is, in particular, methyl, or secondly ethyl, propyl, isopropyl or butyl, or furthermore iso- or secondary butyl.

Phenyl-$C_4$-$C_7$alkyl is, for example, straight-chain phenyl-$C_4$-$C_7$alkylene, in particular $\omega$-phenyl-$C_4$-$C_6$alk-1-yl, such as 4-phenylbut-1-yl, 5-phenylpent-1-yl or 6-phenylhex-1-yl, or further 3-phenylbut-1-yl or 4-phenylpent-1-yl.

Phenyl-$C_4$-$C_7$alkenyl is, for example, straight-chain phenyl-$C_4$-$C_7$alkenyl, in particular such a radical in which the double bond is in a position higher than the $\alpha,\beta$-position relative to the N atom, such as 4-phenylbut-3-en-1-yl, 4-phenylbut-2-en-1-yl or 5-phenylpent-4-en-1-yl.

$C_2$-$C_4$Alkenyl is, for example, vinyl, allyl or buten-2-yl.

$C_2$-$C_4$Alkylene is, for example, straight-chain $C_2$-$C_4$alkylene, in particular straight-chain $C_2$-$C_3$alkylene, such as $\alpha,\omega$-$C_2$-$C_4$alkylene, for example ethylene, 1,3-propylene or, secondly, 1,4-butylene.

Salts of compounds of the formula I are in particular inner salts thereof or salts with pharmaceutically acceptable bases, such as non-toxic metal salts derived from metals of groups Ia, Ib, IIa and IIb, for example alkali metal salts, in particular sodium or potassium salts, alkaline earth metal salts, in particular calcium or magnesium salts, copper, aluminium or zinc salts and also ammonium salts with ammonia or organic amines, or quaternary ammonium bases, such as aliphatic amines, which may be C-hydroxylated, in particular mono-, di- or tri-lower alkylamines, for example methyl-, ethyl-, dimethyl- or diethylamine, mono-, di- or tri-(hydroxy-lower alkyl)-amines, such as ethanol-, diethanol- or triethanolamine, tris(hydroxymethyl)-aminomethane or 2-hydroxy-tert-butylamine, or N-(hydroxy-lower alkyl)-N,N-di-lower alkylamines or N-(polyhydroxy-lower alkyl)-N-lower alkylamines, such as 2-(dimethylamino)-ethanol or D-glucamine, or quaternary aliphatic ammonium hydroxides, for example with tetrabutylammonium hydroxide. Both complete and partial salts, i.e. salts having 1, 2, 3 or 4, preferably 2, equivalents of base per mole of the acid of the formula I, are included.

The compounds of the formula I and their salts display useful pharmacological properties. In particular, they have a pronounced regulating action on calcium metabolism in warm-blooded animals.

In particular, they cause a pronounced inhibition of bone resorption in the rat, which can be demonstrated both in the experimental design according to Acta Endocrinol. 78, 613-24 (1975) with the aid of the PTH-induced increase in the serum calcium level following subcutaneous administration in doses of about 0.01 to about 1.0 mg/kg, and in the TPTX (thyroparathyroidectomized) rat model with the aid of the experimental hypercalcaemia caused by vitamin $D_3$, after administration of doses of about 0.001 to 0.01 mg subcutaneously. Tumour hypercalcaemia caused by Walker-256 tumours are likewise inhibited after peroral administration of about 1.0 to about 100 mg/kg. They furthermore exhibit a clear inhibition on the progress of chronic arthritic processes of adjuvant arthritis in rats in doses of about 0.01 to 1.0 mg/kg subcutaneously in the experimental design according to Newbould, Brit. J. Pharmacology 21, 127 (1963) and according to Kaibara et al., J. Exp. Med. 159, 1388-96 (1984). They are therefore outstandingly suitable as medicament active ingredients for the treatment of diseases which can be associated with disturbances in calcium metabolism, for example inflammatory processes in joints, degenerative processes in the articular cartilage, osteoporosis, periodontitis, hyperparathyroidism and calcium deposits in blood vessels or on prosthetic implants. Both diseases in which an abnormal deposition of sparingly soluble calcium salts is to be found and those from the arthritis sphere, for example Bechterew's disease, neuritis, bursitis, periodontitis, tendinitis, fibrodysplasia, osteoarthrosis or arteriosclerosis, as well as those where abnormal dissolving of hard body tissue is in the foreground, such as hereditary hypophosphatasia, degenerative processes in the articular cartilage, osteoproroses of various origins, Paget's disease and osteodystrophia fibrosa, as well as osteolytic processes caused by tumours are favourably influenced.

The invention particularly relates to compounds of the formula I in which $R_1$ is phenyl-$C_4$-$C_7$alkyl or phenyl-$C_4$-$C_7$alkenyl, $R_2$ is $C_1$-$C_4$alkyl or $C_1$-$C_4$alkenyl and alk is $C_2$-$C_4$alkylene, and their salts, in particular pharmaceutically acceptable salts.

The invention especially preferably relates to compounds of the formula I in which $R_1$ is straight-chain phenyl-$C_4$-$C_7$alkyl, such as 4-phenylbut-1-yl, 5-phenylpent-1-yl or 6-phenylhex-1-yl, $R_2$ is $C_1$-$C_4$alkyl, such as methyl, and alk is $C_2$-$C_3$alkylene, such as ethylene, and their salts, in particular pharmaceutically acceptable salts.

The invention primarily relates to compounds of the formula I in which $R_1$ is straight-chain $\omega$-phenyl-$C_4$-$C_6$alk-1-yl, such as 4-phenylbut-1-yl or 5-phenylpent-1-yl, alk' is straight-chain $C_2$-$C_4$alkylene, $R_2$ is $C_1$-$C_4$alkyl and alk is $C_2$-$C_3$alkylene, such as ethylene, and their salts, in particular pharmaceutically acceptable salts.

The invention specifically relates to the compounds of the formula I mentioned in the examples and their salts, in particular their inner salts and pharmaceutically acceptable salts with bases.

The invention furthermore relates to a process, which is based on methods known per se, for the preparation of compounds of the formula I and their salts. This comprises a) converting functionally modified phosphono $X_1$ and if appropriate $X_2$ in a compound of the formula

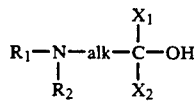

in which $X_1$ is a functionally modified and $X_2$ is a free or functionally modified phosphono group, into the free phosphono group, or b) reacting compounds of the formulae

and

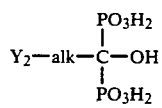

in which one of the radicals $Y_1$ and $Y_2$ is a reactive esterified hydroxyl group and the other is a group of the formula —$N(R_B)$—H, in which one of the radicals $R_A$ and $R_B$ is a radical $R_1$ and the other is a radical $R_2$, or salts thereof with one another, or reacting compounds of the formulae

and

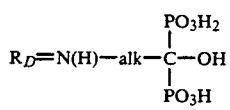

in which $R_C$ is a divalent radical corresponding to the radical $R_1$, for example a phenyl-$C_4$-$C_7$alkylidene radical or phenyl-$C_4$-$C_7$alkenylidene radical, and $R_D$ is a radical $R_2$, or $R_C$ is a divalent radical corresponding to the radical $R_2$, for example $C_1$-$C_4$alkylidene, and $R_D$ is a radical $R_1$, with one another under reducing conditions, or c) reacting a compound of the formula

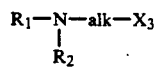

in which $X_3$ is carboxyl, carbamyl or cyano, in particular carboxyl or cyano, with a phosphorylating agent, hydrolyzing the primary product and replacing the amino group in an intermediate product, obtained from compounds of the formula V in which $X_3$ is cyano or carbamyl, of the formula

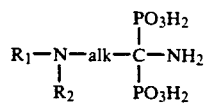

or a salt thereof, by hydroxyl by treatment with nitrous acid, and if desired converting a resulting compound into another compound of the formula I and/or converting a resulting free compound into a salt or a resulting salt into the free compound or into another salt.

Functionally modified phosphono groups to be converted into phosphono according to process variant a) are, for example, in an ester form, in particular a diester form of the formula —$P(=O)(OR)_2$(IIa), in which OR is etherified hydroxyl, for example lower aloxy, lower alkanoyloxy-lower alkoxy, such as $C_2$-$C_7$alkanoyloxy-$C_1$-$C_4$alkoxy, for example acetyl- or pivaloyloxymethyl, or a phenyloxy- or α-phenyl-lower alkoxy group or silyloxy, such as tri-lower alkylsilyloxy, which is unsubstituted or substituted by lower alkyl, lower alkoxy, halogen, trifluoromethyl and/or hydroxyl.

The conversion of functionally modified phosphono groups into free phosphono groups is carried out in the customary manner, such as by hydrolysis, for example in the presence of a mineral acid, such as hydrochloric or sulfuric acid, at about 80° C. to about 110° C., for example at the boiling point, or by reaction with a tri-lower alkyl-halogenosilane, for example with trimethylchlorosilane or in particular trimethyl-iodosilane or trimethyl-bromosilane, preferably in methylene chloride in the temperature range from about 0° to about 40° C., and subsequent reatment with water. α-Phenyl-lower alkyl esters can furthermore be converted into compounds of the formula I by hydrogenolysis, for example reaction with hydrogen in the presence of a hydrogenation catalyst, such as a nickel or noble metal catalyst, for example palladium-on-charcoal, preferably in a lower alkanol, under normal pressure and temperature conditions.

The starting substances of the formula II can be prepared for example, by reacting a compound of the formula

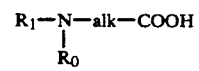

in which $R_0$ is a radical $R_2$ or an amino-protective group, or preferably the anhydride or acid chloride thereof, with a corresponding phosphorous acid triester of the formula $P(OR)_3$(IIc), for example at 0° C. to about 60° C., to give a compound of the formula

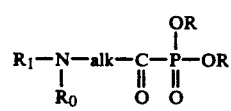

and further reacting this with a phosphorous acid diester of the formula H—$P(=O)(OR)_2$ (IIe) or $P(OH)(OR)_2$ (IIf) in the presence of a di-lower alkylamine, for example diethylamine, or an alkali metal lower alkanolate, for example sodium methylate, to give the corresponding compound of the formula

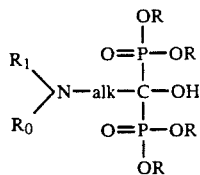

if appropriate splitting off the amino-protective group and introducing the radical $R_2$, for example as described below under b). Where they are not known, starting substances of the formula IIb can be prepared, for example, by reacting a corresponding compound of the formula $$R_1—N(R_0)—H \qquad (IIh)$$

in which $R_0$ is a group $R_2$ or an amino-protective group, with a compound of the formula $$Y—alk—COOR \qquad (IIi)$$

in which Y is halogen, such as bromine, or to prepare compounds IIb in which alk is 1,2-lower alkylene, for example ethylene, with a compound of the formula $$alk_0—COOR \qquad (IIj)$$

in which $alk_0$ is lower alk-1-enyl, in each case hydrolyzing the resulting ester to give the acid, anhydrizing or chlorinating this, for example by means of phosphorus pentachloride, and if desired splitting off the amino-protective group, if present.

Reactive esters (III) or (IV) to be used according to process variant b) contain as the reactive esterified hydroxyl group, for example, a halogen, such as chlorine, bromine or iodine atom, or a sulfonyloxy group, such as alkane- or unsubstituted or substituted benzenesulfonyloxy, for example methane- or p-toluenesulfonyloxy.

The reaction with the reactive esters mentioned is carried out, for example, in the presence of a base, such as an alkali metal hydroxide or alkaline earth metal hydroxide, for example sodium hydroxide, or a quaternary ammonium hydroxide, for example tetrabutylammonium hydroxide, advantageously in the presence of a solvent or diluent, for example a lower alkanol, di-(lower alkyl) ketone or cycloaliphatic ether, for example isopropanol, methyl ethyl ketone, dioxane or tetrahydrofuran.

The reaction with oxo compounds IIIa is carried out, for example, in the presence of a suitable reducing agent, such as an alkali metal borohydride, for example sodium cyanoborohydride, or in particular formic acid. A compound of the formula IVa in which $R_D$ is a radical $R_1$ can be reacted, in particular, with a lower alkanal, for example with formaldehyde, and formic acid under reducing conditions to give the corresponding compound of the formula I in which $R_2$ is lower alkyl, for example methyl. Alternatively, lower alkyl or lower alkenyl $R_2$ can also be introduced by reaction with a reactive ester of a lower alkanol or lower alkenol in the customary manner, preferably in the presence of a basic condensing agent, such as an alkali metal lower alkanolate.

The starting substances of the formula IV can be prepared, for example, by reacting a compound of the formula $$Y_2—alk—COOH \qquad (IVa)$$

with phosphorous acid and phosphorus trichloride or with phosphoric acid and an excess of phosphorus tribromide in the customary manner, for example in chlorobenzene, and then working up the mixture hydrolytically.

Examples of suitable phosphorylating agents for process variant c) are phosphorus trioxide, phosphorus trihalides mixed with phosphorous acid or phosphoric acid, phosphorus oxychloride, phosphorus pentachloride or phosphorus trichloride and chlorine. Phosphorus trioxide is preferred, and is preferably formed in situ by reaction of phosphorus trichloride with phosphorous acid or by reaction of excess phosphorus trichloride with aqueous phosphoric acid, for example with commercially available approximately 75% to approximately 95%, preferably approximately 85%, phosphoric acid. The reaction is advantageously carried out by heating, for example to about 70° to about 120° C., in a suitable solvent, such as tetrachloroethane, trichloroethane, chlorobenzene, chlorotoluene or paraffin oil, with hydrolytic working up.

The treatment of intermediate products of the formula VI with nitrous acid is carried out in the customary manner by liberating the latter in aqueous solution from one of its salts, for example from sodium nitrite, by acid treatment, for example the action of hydrochloric acid, a corresponding unstable diazonium salt, for example chloride, which splits off nitrogen, the α-hydroxyl group being introduced, being intermediately formed.

Where they are not known, the starting substances of the formula V can be prepared, for example, by reacting a corresponding compound of the formula $$R_1—N(R_2)—H \qquad (IIh)$$

with a compound of the formula $$Y—alk—X_3 \qquad (IIi)$$

in which Y is halogen, such as bromine, or to prepare compounds of the formula V in which alk is 1,2-lower alkylene, for example ethylene, with a compound of the formula $$alk_0—X_3 \qquad (IIf)$$

in which $alk_0$ is a lower alk-1-enyl radical, in each case splitting off the amino-protective group, if present, and if desired in each case hydrolyzing the resulting primary product to give the acid.

Compounds of the formula I obtained according to the process or by another process known per se can be converted into other compounds of the formula I in a manner known per se.

Thus, non-aromatic double bonds present in $R_1$ and/or $R_2$ can be reduced to single bonds in the customary manner by hydrogenolysis, for example reaction with hydrogen in the presence of a hydrogenation catalyst, such as a nickel or noble metal catalyst, for example palladium-on-charcoal, preferably in a lower alkanol under normal pressure and temperature conditions.

Depending on the choice of the starting substances and procedures, the novel compounds can be in the form of one of the possible isomers or as a mixture thereof, for example, depending on the number of asymmetric carbon atoms, as pure optical isomers, such as antipodes, or as isomer mixtures, such as racemates, diastereoisomer mixtures or racemate mixtures.

The diastereomer mixtures and racemate mixtures obtained can be resolved into the pure isomers, diastereomers or racemates in a known manner on the basis of the physico-chemical differences of the constituents, for example by chromatography and/or fractional crystallization.

Resulting racemates can furthermore be resolved into the optical antipodes by known methods, for example by recrystallization from an optically active solvent, with the aid of microorganisms or by reaction of an acid end product with an optically active base which forms salts with the racemic acid and resolution of the salts obtained in this manner, for example on the basis of their different solubilities, into the diasteromers, from which the antipodes can be liberated by the action of suitable agents. The more active of the two antipodes is advantageously isolated.

Resulting free compounds of the formula I, including their inner salts of the formula I, can be converted into base salts by partial or complete neutralization with one of the abovementioned bases. Acid addition salts can also be converted into the corresponding free compounds of inner salts thereof in analogous manner.

Conversely, resulting free compounds of the formula I can be converted into acid addition salts by treatment with a proton acid.

Resulting salts can be converted into other salts with a lower cation content (partial salts) or into the free compounds in a manner known per se, for example by treatment with an acid reagent, such as a mineral acid. Resulting free compounds can be converted into salts by treatment with a base, for example alkali metal hydroxide solution, and/or resulting salts with a lower cation content (partial salts) can be converted in the same manner into those with a higher cation content, for example complete salts.

The compounds, including their salts, can also be obtained in the form of their hydrates, or can include the solvent used for the crystallization.

As a result of the close relationship between the novel compounds in the free form and in the form of their salts, by the free compounds or their salts above and below there are also to be understood in the general sense and expediently, where appropriate, the corresponding salts or free compounds.

The invention also relates to those embodiments of the process in which a compound obtainable as an intermediate at any stage of the process is used as the starting substance and the missing steps are carried out, or a starting substance is used, or in particular formed under the reaction conditions, in the form of a salt and/or racemate or antipode.

Those starting substances which lead to the compounds described initially as particularly useful are preferably used in the process according to the present invention. The invention likewise relates to novel starting substances and processes for their preparation.

The pharmaceutical preparations according to the invention which contain compounds of the formula I or pharmaceutically acceptable salts thereof are those for enteral, such as oral or rectal, and parenteral administration which contain the pharmacological active ingredient by itself or together with a pharmaceutically acceptable carrier material.

The novel pharmaceutical preparations contain, for example, from about 10% to about 80%, preferably from about 20% to about 60% of the active ingredient. Pharmaceutical preparations according to the invention for enteral or parenteral administration are, for example, those in dose unit forms, such as sugar-coated tablets, tablets, capsules or suppositories, and furthermore ampoules. These are obtained in a manner known per se, for example by means of conventional mixing, granulating, sugar-coating, dissolving or lyophilizing processes. Thus, pharmaceutical preparations for oral use can be obtained by combining the active ingredient with solid carriers, granulating, if appropriate, a resulting mixture and processing the mixture or granules, if desired or necessary after addition of suitable adjuncts, to tablets or sugar-coated table cores.

Suitable carriers are, in particular, fillers, such as sugars, for example lactose, sucrose, mannitol or sotbitol, and cellulose preparations, and furthermore binders, such as starch mucilage using, for example, maize, wheat, rice or potato starch, gelatin, tragacanth, methylcellulose and/or polyvinylpyrrolidone, and/or, if desired, disintegrating agents, such as the abovementioned starches, and furthermore carboxymethyl-starch, crosslinked polyvinylpyrrolidone, agar and alginic acid or a salt thereof, such as sodium alginate. Adjuncts are, in particular, glidants and lubricants, for example silicic acid, talc, stearic acid and/or polyethylene glycol. Sugar-coated tablet cores are provided with suitable coatings, which may be resistant to gastric juice, substances used being, amongst others, concentrated sugar solutions, which may contain gum arabic, talc, polyvinylpyrrolidone, polyethylene glycol and/or titanium dioxide, lacquer solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate. Dyes or pigments can be added to the tablets or sugar-tablet coatings, for example for identification or for characterization of different active ingredient doses.

Other pharmaceutical preparations for oral use are dry-filled capsules of gelatin, and soft, closed capsules of gelatin and a plasticizer, such as glycerol or sorbitol. The dry-filled capsules can contain the active ingredient in the form of granules, for example mixed with fillers, such as lactose, binders, such as starches, and/or lubricants, such as talc, and if appropriate stabilizers. In soft capsules, the active ingredient is preferably dissolved or suspended in suitable liquids, such as fatty oils, paraffin oil or liquid polyethylene glycols, it likewise being possible to add stabilizers.

Possible pharmaceutical preparations for rectal use are, for example, suppositories which consist of a combination of the active ingredient with a suppository base. Examples of suitable suppository bases are naturally occurring or synthetic triglycerides, paraffin hydrocarbons, polyethylene glycols or higher alkanols. It is furthermore also possible to use gelatin rectal capsules which contain a combination of the active ingredient with a base; possible bases are, for example, liquid triglycerides, polyethylene glycols or paraffin hydrocarbons.

Compositions which are suitable for parenteral administration are, in particular, aqueous solutions of an active ingredient in water-soluble form, for example a water-soluble salt, and furthermore suspensions of the active ingredient, such as corresponding oily injection suspensions, suitable lipophilic solvents or vehicles, such as fatty oils, for example sesame oil, or synthetic fatty acid esters, for example ethyl oleate or triglycerides, being used, or aqueous injection suspensions which contain viscosity-increasing substances, for example sodium carboxymethylcellulose, sorbitol and/or dextran and if appropriate also stabilizers.

The present invention likewise relates to the use of the compounds of the formulae I and their salts, preferably for the treatment of diseases to be attributed to disturbances in calcium metabolism, for example of the rheumatic type and in particular of osteoporoses.

Dosages below 0.01 mg/kg of body weight have only an insignificant influence on pathological calcification or the dissolving of hard tissues. At dosages of more than 100 mg/kg of body weight, long-term toxic side effects may occur. The compounds of the formula I and their salts can be administered either orally, or subcutaneously, intramuscularly or intravenously in a hypertonic solution. The preferred daily dose for these uses is in the range from about 0.1 to 5 mg/kg for oral use, in the range from about 0.1 to 1 mg/kg for subcutaneous and intramuscular administration and in the range from about 0.01 to 2 mg/kg, for example from about 0.013 to 0.67 mg/kg, for intravenous administration.

However, the dosage of the compounds used can be varied and depends on the particular conditions, such as the nature and severity of the disease, the duration of the treatment and the particular compound. Individual doses contain, for example, from 0.01 to 10 mg, and dose unit forms for parenteral administration, such as intravenous administration, contain, for example, from 0.01 to 0.1 mg, preferably 0.02 to 0.08 mg, and oral dose unit forms contain, for example, from 0.2 to 2.5 mg, preferably 0.3 to 1.5 mg per kg of body weight. The preferred individual dosage is 10 to 100 mg for oral administration and 0.5 to 5 mg for intravenous administration and can be administered up to 4 times daily. The higher dosages for oral administration are necessary because of the limited absorption. For longer-lasting treatments, after an initially higher dosage, the dosage can usually be changed to lower dosages in order to maintain the desired effect.

EXAMPLE 1

12.75 g (0.0446 mol) of 3-[N-(5-phenylpentyl)-N-methylamino]-propionic acid hydrochloride are heated under reflux at 100° with 6.1 ml of 85% phosphoric acid and 30 ml of chlorobenzene, while stirring. 11.7 ml of phosphorus trichloride are then added dropwise at 100°, evolution of the gas taking place. The reaction mixture precipitates a thick mass in the course of 30 minutes. The mixture is heated at 100° for a further 3 hours and the supernatant chlorobenzene is then decanted off. The viscous mass which remains is heated at the boil under reflux with 45 ml of 9N hydrochloric acid for 3 hours, while stirring. It is filtered hot, with addition of charcoal, and the filtrate is concentrated under reduced pressure. Addition of acetone gives the crude 3-[N-(5-phenylpentyl)-N-methyl-amino]-1-hydroxypropane-1,1-diphosphonic acid, which is recrystallized from water: melting point 124°-127° (decomposition).

Disodium 3-[N-(5-phenylpentyl)-N-methylamino]-1-hydroxy-propane-1,1-diphosphonate is obtained by dissolving 0.005 mol of the product in 10 ml N sodium hydroxide solution, concentrating the solution under reduced pressure and crystallizing the product, with addition of methanol.

The 3-[N-(5-phenylpentyl)-N-methylamino]-propionic acid hydrochloride used as the starting material can be prepared as follows:

10.0 g (0.056 mol) of N-(5-phenylpentyl)-N-methylamine are dissolved in 40 ml of diethyl ether and 6.7 g of ethyl acrylate are added. After the mixture has been left to stand at room temperature for 4 days, the ether is distilled off. The oil which remains is crude ethyl 3-[N-(5-phenylpentyl)-N-methylamino]-propionate.

14.2 g (0.05 mol) of the ester obtained as above are heated under reflux with 80 ml of 4N hydrochloric acid for 24 hours. The mixture is then evaporated completely under reduced pressure and the crystalline residue is triturated with acetone. Filtration with suction, washing and drying of the crystals gives 3-[N-(5-phenylpentyl)-N-methylamino]-propionic acid hydrochloride of melting point 97°-99°.

EXAMPLE 2

0.9 g (2.45 mmol) of 3-(4-phenylbutylamino)-1-hydroxypropane-1,1-diphosphonic acid is boiled under reflux with 7.5 ml of 98% formic acid and 0.5 ml of 35% aqueous formaldehyde solution for 20 hours, while stirring.

The reaction mixture is concentrated under reduced pressure and the residue is crystallized from methanol. 3-[N-(4-Phenylbutyl)-N-methylamino]-1-hydroxypropane-1,1-diphosphonic acid is obtained, melting point 128°-132° (decomposition).

The starting material can be prepared, for example, as follows:

Starting from N-(4-phenylbutyl)-N-benzylamine and ethyl acrylate, ethyl 3-[N-(4-phenylbutyl)-N-benzylamino]-propionate is obtained analogously to Example 1 and is hydrolyzed with hydrochloric acid to give 3-[N-(4-phenylbutyl)-N-benzylamino]-propionic acid hydrochloride, melting point 145°-147°.

27.13 g (0.085 mol) of this hydrochloride are hydrogenated in 300 ml of ethanol over 3 g of 5% palladium-on-charcoal catalyst at 20°-25° under normal pressure until the uptake of hydrogen has ended. The catalyst is filtered off with suction, the filtrate is evaporated and the residue is crystallized from acetone. 3-[N-(4-Phenylbutyl)-amino]-propionic acid hydrochloride is obtained, melting point 135°-137°.

3-(4-Phenylbutylamino)-1,1-hydroxypropane-1,1-diphosphonic acid is obtained analogously to Example 1 from 3-N-(4-phenylbutylamino)-propionic acid hydrochloride, melting point 191°-193° (decomposition).

EXAMPLE 3

3-[N-(6-Phenylhexyl)-N-methylamino]-1-hydroxypropane-1,1-diphosphonic acid, melting point 149°-152° (decomposition) can be prepared in a manner analogous to that described in Example 2 via 3-[N-(6-phenylhexyl)amino]-propionic acid hydrochloride, melting point 128°-129°, and 3-[N-(3-phenylhexyl)-amino]-1-hydroxy-propane-1,1-diphosphonic acid, melting point 203°-205° (decomposition).

EXAMPLE 4

3-[N-(7-Phenylheptyl)-N-methylamino]-1-hydroxypropane-1,1-diphosphonic acid, melting point 138°-142° (decomposition), can be prepared in a manner analogous to that described in Example 1 via 3-[N-(7-phenylheptyl)-N-methylamino]-propionic acid hydrochloride, melting point 95°–97°.

EXAMPLE 5

Tablets containing 75 mg of active ingredient, for example 3-[N-(5-phenylpentyl)-N-methylamino]-1-hydroxypropane-1,1-diphosphonic acid or a salt, for example the disodium salt, thereof, can be prepared as follows:

| Constituents (for 1000 tablets) | |
| --- | --- |
| Active ingredient | 75.0 g |
| Lactose | 268.5 g |
| Maize starch | 22.5 g |
| Polyethylene glycol 6000 | 5.0 g |
| Talc | 15.0 g |
| Magnesium stearate | 4.0 g |
| Demineralized water | q.s. |

PREPARATION

The solid ingredients are first forced through a sieve of 0.6 mm mesh width. The active ingredient, lactose, talc, magnesium stearate and half the starch are then intimately mixed. The other half of the starch is suspended in 65 ml of water and this suspension is added to a boiling solution of the polyethylene glycol in 260 ml of water. The resulting mucilage is added to the pulverulent substances, the entire components are mixed and the mixture is granulated, if necessary with the addition of water. The granules are dried at 35° overnight, forced through a sieve of 1.2 mm mesh width and pressed to tablets which are concave on both sides and have a diameter of about 10 mm and a breaking notch on the upper side.

EXAMPLE 6

Tablets containing 10 mg of active ingredient, for example 3-[N-(5-phenylpentyl)-N-methylamino]-1-hydroxypropane-1,1-diphosphonic acid, or a salt, for example the disodium salt thereof, can be prepared as follows:

| Composition (for 1000 tablets) | |
| --- | --- |
| Active ingredient | 10.0 g |
| Lactose | 328.5 g |
| Maize starch | 17.5 g |
| Polyethylene glycol 6000 | 5.0 g |
| Talc | 25.0 g |
| Magnesium stearate | 4.0 g |
| Demineralized water | q.s. |

PREPARATION

The solid ingredients are first forced through a sieve of 0.6 mm mesh width. The active ingredient, lactose, talc, magnesium stearate and half the starch are then intimately mixed. The other half of the starch is suspended in 65 ml of water and this suspension is added to a boiling solution of the polyethylene glycol in 260 ml of water. The resulting mucilage is added to the pulverulent substances, the entire components are mixed and the mixture is granulated, if necessary with the addition of water. The granules are dried overnight at 35°, passed through a sieve of 1.2 mm mesh width and pressed to tablets which are concave on both sides and have a diameter of about 10 mm and a breaking notch on the upper side.

EXAMPLE 7

Gelatin dry-filled capsules containing a 100 mg of active ingredient, for example 3-[N-(5-phenylpentyl)-N-methylamino]-1-hydroxypropane-1,1-diphosphonic acid or a salt, for example the disodium salt thereof, can be prepared as follows:

| Composition (for 1000 capsules) | |
| --- | --- |
| Active ingredient | 350.0 g |
| Microcrystalline cellulose | 30.0 g |
| Sodium lauryl sulfate | 2.0 g |
| Magnesium stearate | 8.0 g |

The sodium lauryl sulfate is sieved through a sieve of mesh width 0.2 mm into the active ingredient (lyophilized) and the two components are intimately mixed for 10 minutes. The microcrystalline cellulose is then sieved through a sieve of mesh width 0.9 mm and the components are intimately mixed again for 10 minutes. Finally, the magnesium stearate is sieved through a sieve of mesh width 0.8 mm, and after mixing for a further 3 minutes 390 mg portions of the mixture are introduced into size O (elongated) gelatin dry-filled capsules.

EXAMPLE 8

A 0.2% injection or infusion solution can be prepared, for example, as follows.

| | |
| --- | --- |
| Active ingredient, for example 3-[N-(5-phenylpentyl)-N-methylamino]-1-hydroxy-propane-1,1-diphosphonic acid or one of its salts, for example its disodium salt | 5.0 g |
| Sodium chloride | 22.5 g |
| Phosphate buffer pH = 7.4 | 3000.0 g |
| Water, demineralized | 2500.0 ml |

The active ingredient is dissolved in 1000 ml of water and the solution is filtered through a microfilter. The buffer solution is added and the mixture is made up to 2500 ml with water. To prepare dose unit forms, 1.0 or 2.5 ml portions are introduced into glass or plastic ampoules (each containing 2.0 or 5.0 mg of active ingredient).

I claim:

1. A phenylalkylaminoalkanediphosphonic acid of the formula

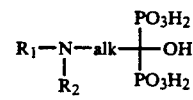

in which $R_1$ is phenyl-$C_4$–$C_6$alkyl, $R_2$ is methyl, and alk represents $C_2$–$C_3$alkylene, or a salt thereof.

2. A compound according to claim 1 of the formula I, in which $R_1$ is straight-chain phenyl-$C_4$–$C_6$alkyl, $R_2$ is methyl and alk is ethylene, or a salt thereof.

3. A compound as claimed in claim 1 being 3-[N-(4-Phenylbutyl)-N-methylamino]-1-hydroxypropane-1,1-diphosphonic acid or a salt thereof.

4. A compound as claimed in claim 1 being 3-[N-(5-Phenylpentyl)-N-methylamino]-1-hydroxypropane-1,1-diphosphonic acid or a salt thereof.

5. A compound as claimed in claim 1 being

3-[N-(6-Phenylhexyl)-N-methylamino]-1-hydroxypropane-1,1-diphosphonic acid or a salt thereof.

6. A pharmaceutical preparation containing a compound according to claim 1 in addition to customary pharmaceutical carriers.

7. A method for the therapeutic treatment of disturbances in calcium metabolism and associated diseases, characterised in that a compound according to claim 1 in the free form or in the pharmaceutically acceptable salt form, is administered to a warm-blooded organism in need of such treatment.

* * * * *